(12) United States Patent
Harmer et al.

(10) Patent No.: US 7,246,617 B1
(45) Date of Patent: Jul. 24, 2007

(54) INHALERS

(75) Inventors: Quentin J. Harmer, Waterbeach (GB);
Stephen W. Eason, Diss (GB);
Matthew N. Sarkar, Cambridge (GB)

(73) Assignee: Vectura Delivery Devices Limited, Bath (GB)

( * ) Notice: Subject to any disclaimer, the term of this patent is extended or adjusted under 35 U.S.C. 154(b) by 45 days.

(21) Appl. No.: 10/018,768

(22) PCT Filed: Jun. 23, 2000

(86) PCT No.: PCT/EP00/05831

§ 371 (c)(1),
(2), (4) Date: Dec. 17, 2001

(87) PCT Pub. No.: WO01/00262

PCT Pub. Date: Jan. 4, 2001

(30) Foreign Application Priority Data

Jun. 23, 1999 (GB) .................................. 9914722

(51) Int. Cl.
A61M 15/00 (2006.01)
A61M 16/00 (2006.01)
B05D 7/14 (2006.01)
B65D 83/06 (2006.01)

(52) U.S. Cl. .................... 128/203.15; 128/200.18; 128/200.22; 128/203.12; 128/203.26

(58) Field of Classification Search .......... 128/203.12, 128/203.15, 203.17, 203.28, 203.26, 203.27, 128/200.18, 200.22; 604/58
See application file for complete search history.

(56) References Cited

U.S. PATENT DOCUMENTS

| 3,726,484 A | 4/1973 | Schurr |
| 3,809,084 A | 5/1974 | Hansen |
| 3,980,074 A | 9/1976 | Watt et al. |
| 4,423,724 A | 1/1984 | Young |
| 4,429,835 A * | 2/1984 | Brugger et al. ............. 239/338 |
| 4,884,565 A | 12/1989 | Cocozza |
| 4,907,583 A | 3/1990 | Wetterlin et al. |
| 5,165,391 A | 11/1992 | Chiesi et al. |
| 5,301,666 A | 4/1994 | Lerk et al. |
| 5,309,900 A * | 5/1994 | Knoch et al. .......... 128/200.14 |
| 5,388,572 A * | 2/1995 | Mulhauser et al. .... 128/203.15 |

(Continued)

FOREIGN PATENT DOCUMENTS

DE 27 22 701 A1 11/1978

(Continued)

OTHER PUBLICATIONS

Hoffmann, A.C., "Effects of Geometry and Solid Loading on the Performance of Gas Cyclones", Power Technology, 70, 1992, pp. 83-91.

(Continued)

*Primary Examiner*—Anhtuan T. Nguyen
*Assistant Examiner*—Michael Mendoza
(74) *Attorney, Agent, or Firm*—Alix, Yale & Ristas, LLP

(57) ABSTRACT

An inhaler comprises a pump 17, a drug dosing device 15 and a cyclone 1 which delivers an aerosol of powdered medicament from the drug dosing device 15 into a chamber 11 when the pump 17 is activated. The aerosol is inhaled by the user through a mouthpiece 13.

7 Claims, 4 Drawing Sheets

U.S. PATENT DOCUMENTS

| | | | |
|---|---|---|---|
| 5,458,135 A | 10/1995 | Patton et al. | |
| 5,476,093 A | 12/1995 | Lankinen | |
| 5,511,538 A * | 4/1996 | Haber et al. | 128/200.14 |
| 5,524,613 A * | 6/1996 | Haber et al. | 128/203.15 |
| 5,546,932 A * | 8/1996 | Galli | 128/203.15 |
| 5,570,686 A * | 11/1996 | Century | 128/203.12 |
| 5,579,760 A | 12/1996 | Kohler | |
| 5,596,982 A | 1/1997 | Blaha-Schnabel | |
| 5,645,050 A * | 7/1997 | Zierenberg et al. | 128/203.15 |
| 5,687,710 A | 11/1997 | Ambrosio et al. | |
| 5,740,794 A | 4/1998 | Smith et al. | |
| 5,755,221 A * | 5/1998 | Bisgaard | 128/203.15 |
| 5,785,049 A | 7/1998 | Smith et al. | |
| 5,875,774 A * | 3/1999 | Clementi et al. | 128/200.18 |
| 6,003,512 A | 12/1999 | Gerde | |
| 6,029,662 A * | 2/2000 | Marcon | 128/203.15 |
| 6,073,629 A * | 6/2000 | Hardy et al. | 128/203.15 |
| 6,347,629 B1 * | 2/2002 | Braithwaite | 128/203.15 |
| 6,367,471 B1 * | 4/2002 | Genosar et al. | 128/200.23 |
| 6,394,085 B1 * | 5/2002 | Hardy et al. | 128/203.15 |
| 6,453,795 B1 * | 9/2002 | Eicher et al. | 92/23 |

FOREIGN PATENT DOCUMENTS

| | | |
|---|---|---|
| EP | 0 407 028 A2 | 1/1991 |
| EP | 1 062 962 A1 | 12/2000 |
| EP | 1 106 196 A2 | 6/2001 |
| FI | 92978 | 5/1995 |
| FR | 1 445 520 | 7/1966 |
| FR | 2 352 556 | 12/1997 |
| GB | 2 344 533 A | 6/2000 |
| WO | WO 90/15635 | 12/1990 |
| WO | WO 91/19524 | 12/1991 |
| WO | WO 92/04066 | 3/1992 |
| WO | WO 92/10229 | 6/1992 |
| WO | WO 93/01891 | 2/1993 |
| WO | WO 94/05360 | 3/1994 |
| WO | WO 94/19041 | 9/1994 |
| WO | WO 98/26827 | 6/1998 |
| WO | WO 99/12597 | 3/1999 |
| WO | WO 99/15217 | 4/1999 |
| WO | WO 99/39761 | 8/1999 |

OTHER PUBLICATIONS

Trefz, M., et al, "Extended Cyclone Theory For Gas Flows with High Solids Concentrations", Chem. Engineering Technology, 16, 1993, pp. 153-160.

Kim, J.C., et al, "Experimental Study of Particle Collection By Small Cyclones", Aerosol Science and Technology, 12, 1990, pp. 1003-1015.

A J Ter Linden, "Investigations into Cyclone Dust Collectors", "Investigations into Cyclone Dust Collectors", IMechE Journal, 1949, 160, 233; pp. 233-251.

P. W. Dietz, "Collection Efficiency of Cyclone Separators", AiChE Journal, 1981, vol. 27, No. 6, pp. 888-892.

D. W. Cooper, "Cyclone Design: Sensitivity, Elasticity and Error Analyses", Atmospheric Environment, 1983, vol. 17, No. 3, pp. 485-489.

R. MCK Alexander, "Fundamentals of Cyclone Design and Operation", Proc. Australas, Inst. Min. Metall., 1949 N. 152-3, pp. 203-228.

Leith, David, et al, "Cyclone Performance and Design", Atmospheric Environment 1973, vol. 7, pp. 527-549.

* cited by examiner

INHALERS

CROSS-REFERENCE TO RELATED APPLICATION

This application is the U.S. National Phase application of International Application No. PCT/EP00/05831 filed Jun. 23, 2000.

SUMMARY OF THE INVENTION

The present invention, at least in its preferred embodiments, seeks to provide an inhaler for generating an inhalable aerosol of a powdered medicament with an effective particle size that is sufficiently small for the medicament to be delivered to and absorbed in the lungs of a patient.

In recent times, there has been a growing interest in the systemic delivery of pharmaceutically-active medicaments via the lung. Such a method of delivery is generally more attractive to the patient than methods such as injection, because it does not involve a needle and can be carried out discreetly in public.

In the case of medicaments in liquid form, the provision of an inhalable aerosol of the medicament can be achieved with a nebuliser or the like. A known device for generating a turbulent airflow in a nebuliser is a so-called "cyclone". The cyclone comprises a cylindrical chamber with an axial outlet and a tangential inlet.

However, for a medicament in solid form, such as crystals, the provision of an inhalable aerosol is more difficult, because it is necessary to achieve a large repeatable dose of fine particles. In order for the particles of medicament to reach the lung and thus be absorbed into the bloodstream, the particles must have an effective diameter approximately in the range 3–5 µm. If the particles are larger than 5 µm they may not be transported by the inhaled airflow deep into the lung, because they are likely to be trapped in the respiratory passages before reaching the deep lung. For example, particles of the order of 10 µm are unlikely to progress further than the trachea and particles of the order of 50 µm tend to deposit on the back of the throat when inhaled. Furthermore, if the particles are less than 1 µm in effective diameter, the particles may not be absorbed in the lung, because they are small enough to be expelled from the lung with the exhaled airflow.

Thus, it will be seen that it is important that the powdered medicament is delivered with an accurately controlled range of particle size in order that it is absorbed effectively in the lung.

It is known for the powdered medicament to be mixed with an excipient (an inert substance, such as lactose, which is combined with the medicament to prepare a convenient dosage form) of relatively large particle size, for example 50–100 µm, to improve the handling properties of the medicament. The medicament attaches electrostatically to the surface of the excipient. In some cases, the particles of medicament agglomerate to form particles of a larger effective diameter. In either case, it is necessary to separate the medicament particles from the excipient and from each other in order to provide an inhalable aerosol which will deliver the medicament for absorption through the lung.

In order to separate the particles, shear forces must be generated between the particles, for example by providing a substantial velocity gradient across the particles. This may be done, for example, by forcing the powder through a narrow nozzle at high speed or introducing the powder into a turbulent air stream.

In traditional metered dose inhalers (MDIs) it is common for the emitted dose (the amount of medicament that enters the patient's airway) to be around 80–90% of the dose ejected from the inhaler. The respirable dose (the amount of medicament that reaches the lung) may be only around 50% of the emitted dose. However, the variation in the respirable dose of known inhalers can be ±20–30%. Such variation may be acceptable in the case of asthma drugs and the like, but when the medicament is a more potent drug such as insulin, growth hormone or morphine, this amount of variability in the dosing is unacceptable. The relatively low respirable dose also represents a significant wastage of what may be an expensive drug. Furthermore, there may be side effects if the proportion of the emitted dose which is not respired is swallowed.

Thus, it is important for the systemic delivery of medicaments by inhalation that a repeatable dose of fine particles can be produced.

It is known for so-called "spacers" to be used in the generation of the aerosol from a metered dose inhaler. The spacer fits onto the mouthpiece of the inhaler and comprises a chamber into which the dose of medicament is ejected by the inhaler. The patient is then able to inhale the dose from the spacer through a corresponding mouthpiece on the spacer.

Large volume spacers are used where the patient is unable to inhale at the same time as operating the metered dose inhaler due to a lack of coordination. Small volume spacers are used to trap large particles which would stick to the back of the throat and may cause undesirable side-effects.

The present invention, at least in its preferred embodiments, seeks to provide an inhaler for generating an inhalable aerosol of a powdered medicament with an effective particle size that is sufficiently small for the medicament to be delivered to and absorbed in the lungs of a patient.

Thus, viewed from a first aspect the invention provides an inhaler comprising:

a chamber having a mouthpiece;

a cyclone arranged to eject an aerosol of medicament into the chamber; and a drug dosing device arranged to provide a dose of powdered medicament entrained in an airflow to the cyclone.

In use of the inhaler, the powdered medicament is entrained in an airflow by the drug dosing device and expelled through the cyclone into the chamber as an aerosol for subsequent inhalation by a patient.

Thus, the invention provides a simple arrangement which can generate an inhalable, fine-particle dose of a dry powder medicament.

In general, the cyclone is configured as a substantially cylindrical cavity provided with a tangential inlet and an axial outlet. The cyclone may be provided with a frusto-conical portion in the region of the outlet for directing the airflow within the cyclone towards the outlet.

In one arrangement, the cyclone is provided with a further axial inlet. The further axial inlet is arranged to introduce the medicament close to the axis of the cyclone to reduce deposition of the medicament on the internal surfaces of the cyclone.

It is desirable for the cyclone to generate as much shear as possible within the airflow. At small radii, close to the axis of the cyclone, the high angular velocities increase the effective viscosity of the air causing a central cylindrical region lying along the axis to rotate as a rigid body within which the shear forces are minimal. Thus, according to an advantageous arrangement, the cyclone is provided with an axial member for directing the medicament towards the walls of the cyclone. In this way, the aerosol is unable to enter the very central zone of the cyclone where the shear forces are at a minimum. Alternatively or in addition, the outlet of the cyclone may be annular to encourage the airflow away from the central axial region of the cyclone.

It is also desirable to reduce the amount of deposition in the chamber of the inhaler and to allow a smaller chamber to be used. Thus, a diffuser may be provided at the outlet of the cyclone. The diffuser may comprise an axial and/or an annular diffuser with a gradual increase in cross-sectional area, preferably with an exponential increase in area for improved diffusion.

A small chamber may be provided at the outlet of the cyclone comparable in volume to the cyclone itself to act as a diffuser. Similarly, a spacer may be provided at the outlet of the cyclone to act as a diffuser.

A plurality of cyclones may be provided such that their outlet flows coincide and interfere with each other to create extra shear forces.

The airflow to the drug dosing device may be provided by an external air source, for example a source of compressed air. In a preferred arrangement, however, the airflow is provided by a pump in the inhaler. Thus, the inhaler may comprise a pump. The pump may be in the form of, for example, a piston pump, a resilient bladder or a source of compressed gas, such as a gas canister. Preferably, the pump is arranged to provide an airflow of repeatable volume and velocity. Thus, the pump may take the form of a spring-powered piston received in a cylinder.

It has been identified that a problem associated with inhalers of the type according to the invention is that when the aerosol is expelled into the chamber, the aerosol tends to interact unfavourably with the air in the chamber. It is known for the chamber to be open and for the air initially within the chamber to be expelled through the mouthpiece of the chamber as the aerosol is introduced through a nozzle. However, this has been found to be unsatisfactory as the amount of medicament which escapes through the mouthpiece before the user inhales is unquantifiable.

Thus, viewed from a further aspect, the invention provides an inhaler comprising:
a chamber having a mouthpiece; and
an aerosolising device having an inlet for taking in an airflow and an outlet for expelling an aerosol into the chamber, wherein the inlet of the aerosolising device is connected to the chamber, such that, in use, the airflow is drawn from the chamber to generate the aerosol.

Thus, according to this aspect of the invention air from within the chamber passes through the aerosolising device to generate the aerosol so that the chamber can be filled with aerosol without expelling air, and potentially medicament, through the mouthpiece of the chamber.

The aerosolising device may comprise a cyclone and/or a drug dosing device as previously described. The aerosolising device may also comprise a pump arranged to draw air from the chamber via the inlet.

In one arrangement, the chamber receives a plunger which is arranged to force air through the aerosolising device as the plunger moves through the chamber. In a particularly preferred embodiment, the aerosolising device is mounted on the plunger.

Thus viewed from a yet further aspect the invention provides an inhaler comprising a chamber having a mouthpiece and a plunger received in the chamber, wherein the plunger is arranged to force air through an aerosolising device to generate an aerosol of medicament in the chamber for inhalation through the mouthpiece.

BRIEF DESCRIPTION OF THE DRAWINGS

Some embodiments of the invention will now be described by way of example only and with reference to the accompanying drawings, in which.

DETAILED DESCRIPTION OF THE PREFERRED EMBODIMENTS

Figure 1:
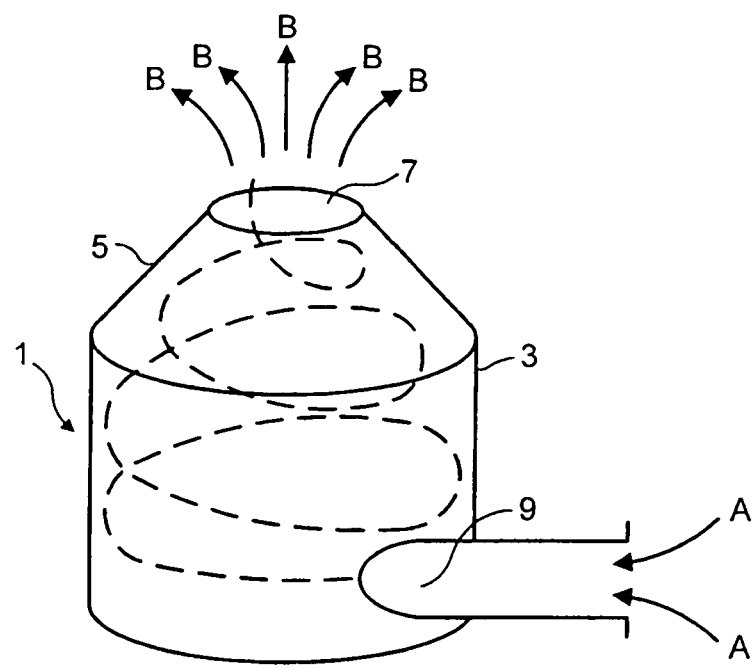
FIG. 1 shows a cyclone for use in the invention.

Corresponding reference numerals have been used for corresponding parts in each embodiment of the invention.

FIG. 1 shows a cyclone 1 for use in aerosolising a powdered medicament according to the invention. The cyclone 1 is in the form of a cylinder 3 of a diameter between about 2 and 15 mm, preferably between 4 and 10 mm. The cylinder 3 is closed at an input end and provided with a frustoconical portion 5 at an output end. The cyclone 1 has an inlet 9 in the region of the closed input end of the cylinder 3, which input 9 is substantially tangential to the wall of the cylinder 3. The frustoconical portion 5 has an outlet 7 defined therein, which outlet 7 is concentric with the axis of the cylinder 3.

In use, an airflow entrains a powdered medicament and enters the cyclone 1 through the tangential inlet 9, as indicated by arrows A. The airflow (and medicament) is directed by the internal surface of the cylinder 3 in a helical path towards the outlet 7. The frustoconical portion 5 of the cyclone 1 narrows the radius of the helical path, thereby increasing the speed of the airflow and increasing the shear forces on the entrained medicament. Consequently, an aerosol of powdered medicament having particles of respirable size issues from the outlet 7 of the cyclone 1, as indicated by arrows B.

Figure 2:
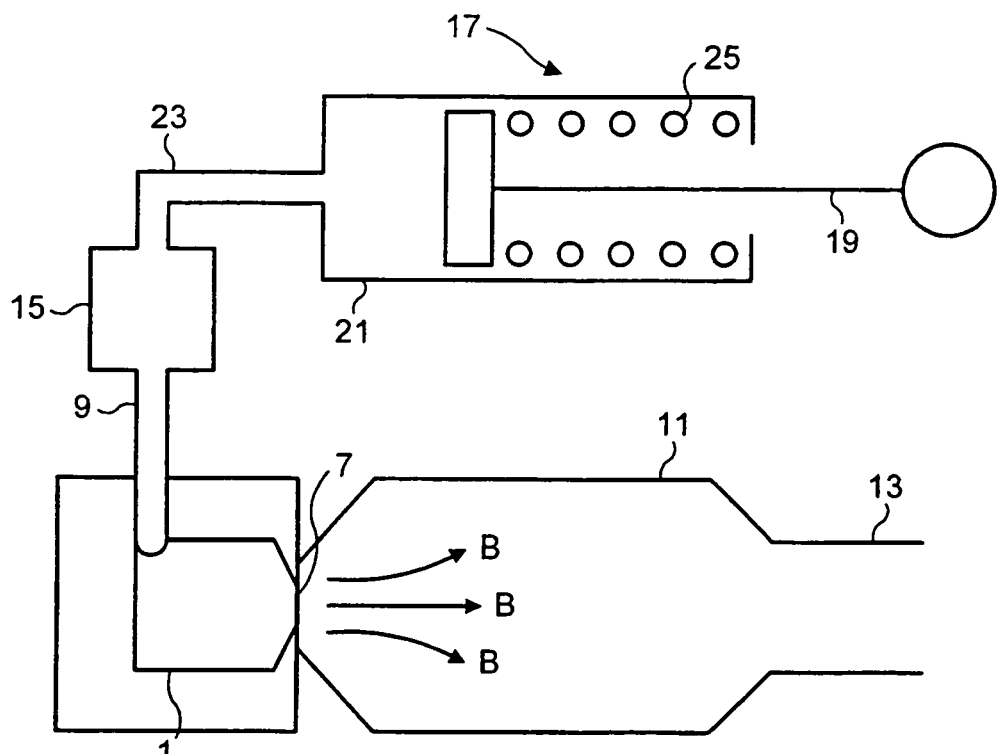
FIG. 2 shows a first embodiment of the invention.
Figure 2A:
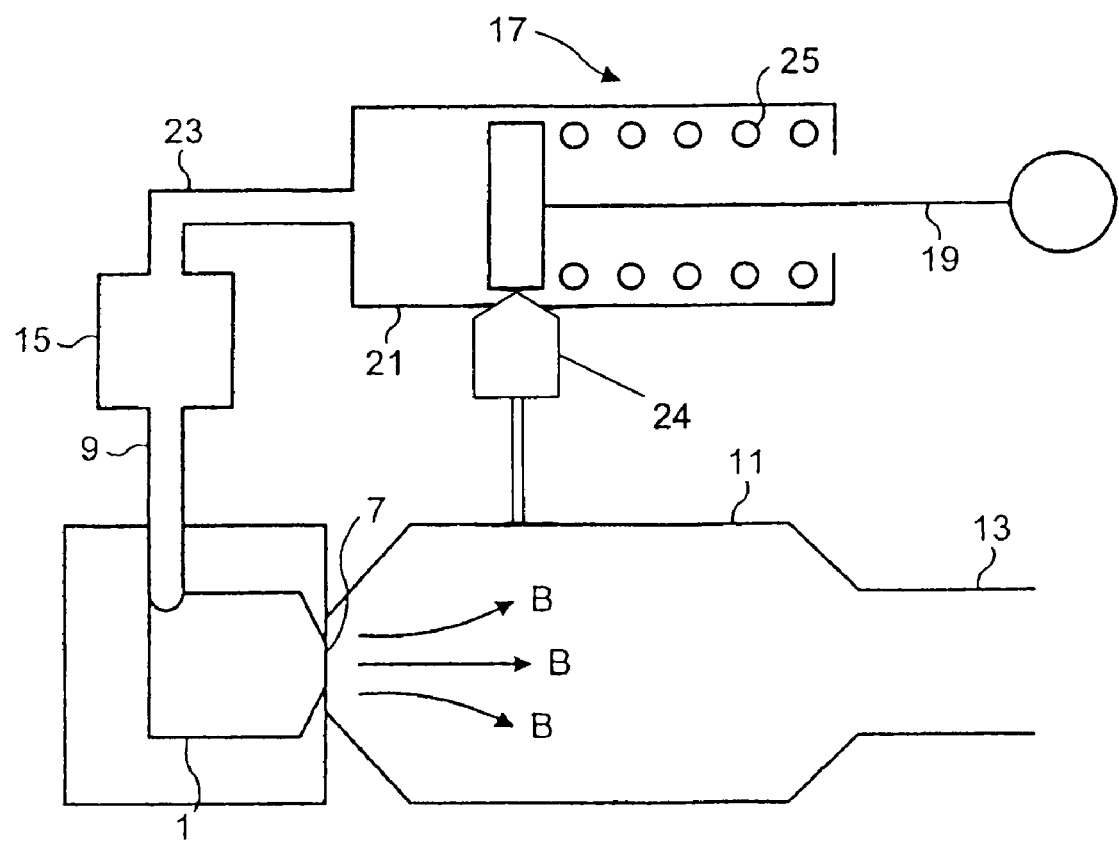
FIG. 2A shows the first embodiment with a breath-activated mechanism.

FIG. 2 shows a first embodiment of the invention. According to this embodiment a cyclone 1 is connected to a chamber 11 having a mouthpiece 13. The chamber has a volume of around 300 ml. The cyclone 1 is located at an end of the chamber 11 opposite the mouthpiece 13, and the outlet 7 of the cyclone 1 is arranged to eject the aerosol of medicament into the chamber 11 towards the mouthpiece 13, as indicated by arrows B.

A drug dosing device 15 is connected to the inlet 9 of the cyclone 1 and is arranged such that, as a flow of air passes through the dosing device 15, a controlled dose of medicament is entrained in the airflow.

The airflow to the drug dosing device 15 is provided by a pump 17, which comprises a plunger 19 received in a pump cylinder 21 and biased towards an outlet 23 of the pump 17 by a spring 25. A breath-actuated mechanism 24 is used to retain the plunger 19 in a retracted position against the biasing force of the spring 25 until the medicament is to be delivered.

In use, this embodiment of the invention operates as follows. The user primes the inhaler by pulling the plunger 19 of the pump 17 into the retracted position where it is retained by the breath-actuated mechanism 24. The user then inhales through the mouthpiece 13 of the chamber 11 and the resultant drop in pressure causes the breath-actuated mechanism to release the plunger 19 which forces a jet of air through the outlet 23 and the drug dosing device 15. The flow of air entrains a measured dose of medicament from the dosing device 15 and carries this dose into the cyclone 1. In the cyclone 1, the dose of medicament is aerosolized, as described in relation to FIG. 1, and is expelled into the chamber 11 through the outlet 7, as indicated by the arrows B. The user is then able to inhale the aerosol of medicament into the deep lung via the mouthpiece 13.

Figure 3:
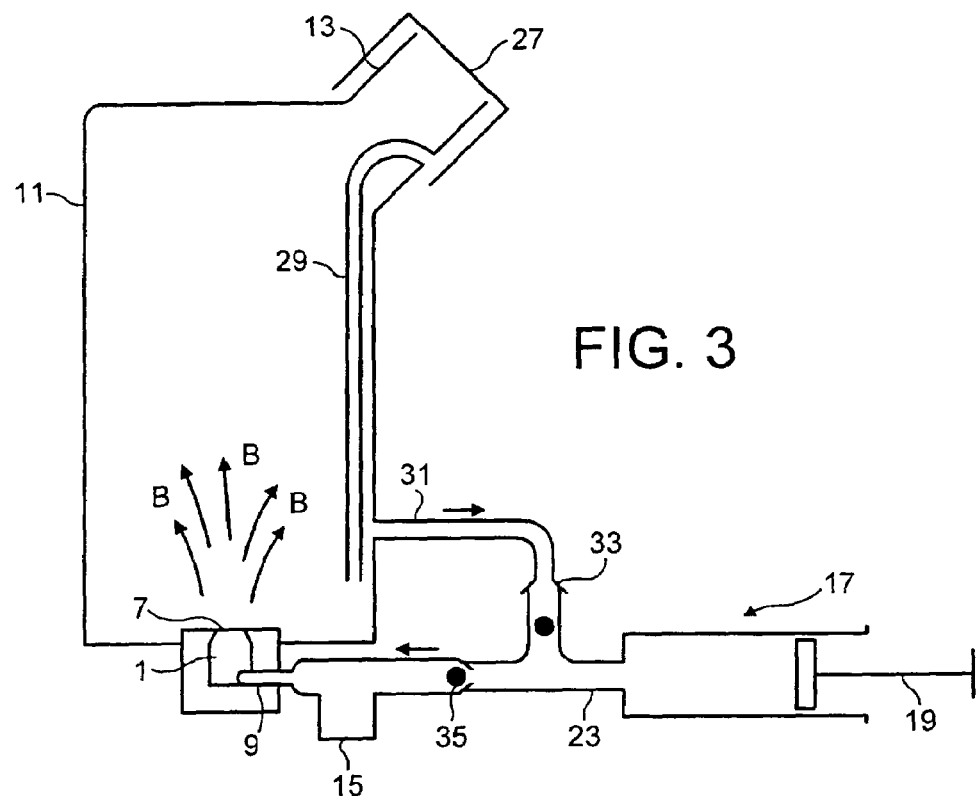
FIG. 3 shows a second embodiment of the invention.

FIG. 3 shows a second embodiment of the invention. In this embodiment, the arrangement of the pump 17, dosing device 15 and cyclone 1 corresponds substantially to that of the embodiment of FIG. 2. However, in this case the chamber 11 is larger than that shown in FIG. 2 and the mouthpiece 13 is offset from the axis of the chamber 11 and of the cyclone 1. The mouthpiece 13 is provided with a cap 27 which closes off the mouthpiece, sealing the chamber 11 from the atmosphere. The cap 27 also closes off an air intake passage 29 which is provided in the chamber 11 to allow air to enter the chamber 11 when the user inhales through the mouthpiece 13. The chamber 11 connects to the outlet 23 of the pump 17 via an air passage 31 and a first non-return valve 33. A second non-return valve 35 is provided between the outlet 23 of the pump 17 and the drug dosing device 15.

In operation of this embodiment, the plunger 19 of the pump 17 is withdrawn (as in the embodiment of FIG. 2) which causes air to be drawn out of the chamber 11 through the air passage 31 and into the pump cylinder 21 via the first non-return valve 33. In this manner, the pressure in the chamber 11 is reduced to below atmospheric. It is to be noted that the release of the plunger 19 in this embodiment is not effected by a breath-actuated device but by a manually actuated release mechanism (not shown). When the release mechanism is actuated, the plunger 19 forces a jet of air through the second non-return valve 35 into the drug dosing device 15 where a measured dose of the medicament is entrained in the air stream. The airflow and entrained medicament pass into the cyclone 1 where the medicament is aerosolised and expelled from the outlet 7 of the cyclone 1 into the chamber 11, as indicated by the arrows B. The reduced pressure in the chamber 11 at this point ensures an even distribution of the aerosol within the chamber 11. The pressure is equalised by the ejection of the aerosol into the chamber 11. Once the aerosol has been delivered into the chamber 11, the user removes the cap 27 and inhales the aerosol through the mouthpiece 13.

Figure 4:
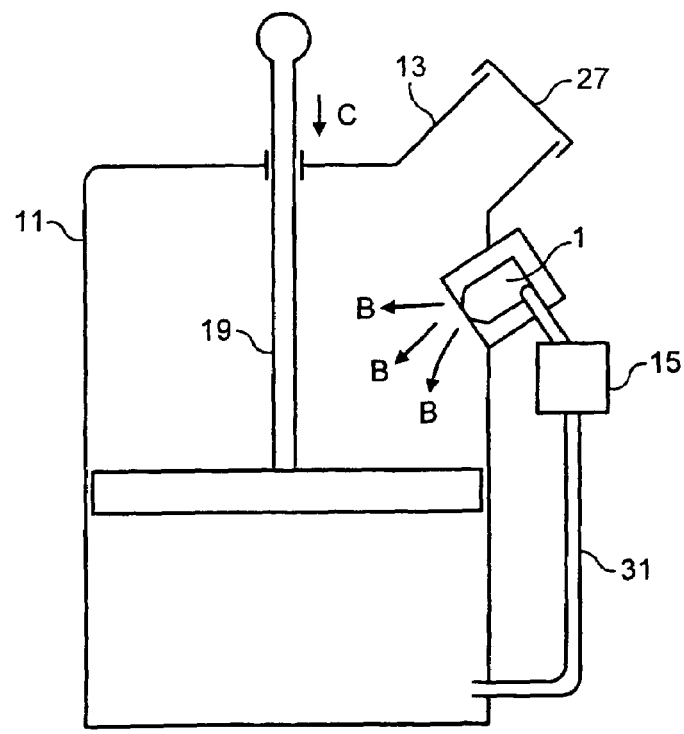
FIG. 4 shows a third embodiment of the invention.

FIG. 4 shows a third embodiment of the invention. According to this embodiment, there is no pump 17, but a plunger 19 is provided within the chamber 11 so that the chamber itself acts as a pump cylinder. Thus, as the plunger 19 is driven in the direction of the arrow C, air is forced out of the chamber 11 through the air passage 31 and into the drug dosing device 15. As the air passes through the drug dosing device 15 it entrains a measured dose of medicament which passes into the cyclone 1 and is aerosolised and expelled into the chamber 11, as indicated by the arrows B. The user inhales the aerosol of medicament by removing the cap 27 and inhaling through the mouthpiece 13.

Figure 5:
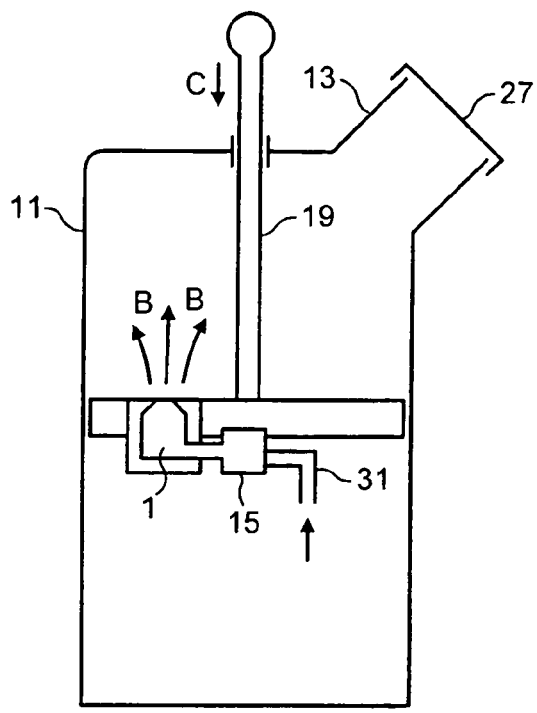
FIG. 5 shows a fourth embodiment of the invention.

FIG. 5 shows a fourth embodiment of the invention according to which the cyclone 1, the drug dosing device 15 and the air passage 31 are mounted on the plunger 19 and are movable therewith such that when the plunger 19 is moved in the direction of the arrow C, air from the lower half of the chamber 11 passes into the air passage 31 and through the drug dosing device 15, so that an aerosol of medicament is expelled from the cyclone 1 into the upper half of the chamber 11, in the direction of the arrows B.

Figure 6:
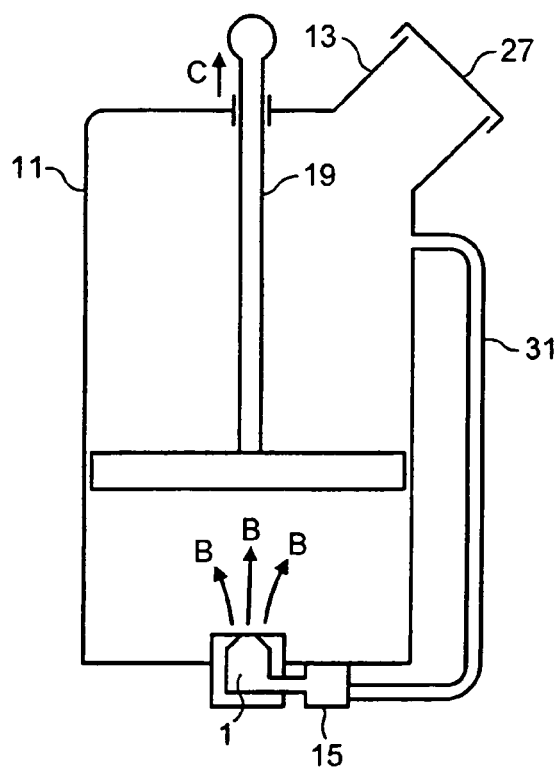
FIG. 6 shows a fifth embodiment of the invention.

FIG. 6 shows a fifth embodiment of the invention which corresponds substantially to that of FIG. 4 except that the cyclone 1 in this embodiment is located in a lower region of the chamber 11 and the direction of movement of the plunger 19 to generate the aerosol is reversed, as indicated by arrow C.

The embodiments of FIGS. 3 to 6 each have the particular advantage that the airflow which is used to entrain the medicament and generate the aerosol via the cyclone 1 is drawn from the chamber 11. Thus, a substantially equal volume of air is withdrawn from the chamber 11 to generate the aerosol as is returned to the chamber 11 when the aerosol is expelled from the cyclone 1. In this way, there is no requirement for the chamber 11 to be vented to atmosphere while the aerosol is generated and there is therefore no risk that any of the medicament will be lost before inhalation by the user.

Although there have been described herein a number of discrete embodiments, the features described in relation to any particular embodiment may be used in combination with the features of other embodiments described herein.

Although the aerosol of medicament has been described herein as an aerosol of powdered medicament in air, the medicament may be dispersed in any other gas or mixture of gases, as required.

The invention claimed is:

1. An inhaler comprising:
   a chamber having a mouthpiece;
   a cyclone configured as a substantially cylindrical cavity provided with a tangential inlet and an axial outlet arranged to eject an aerosol of medicament into the chamber, said cylindrical cavity having a diameter between about 4 and 10 mm;
   a drug dosing device arranged to provide a dose of powdered medicament entrained in an airflow to the cyclone; and
   a piston pump for providing the airflow of repeatable volume and velocity to the drug dosing device, the piston pump comprising a plunger received in a pump cylinder and a spring so that air is drawn into the cylinder when the plunger is withdrawn therefrom against the bias of the spring; and
   a breath-actuated mechanism which retains the plunger in a retracted position against the biasing force of the spring until the medicament is to be delivered.

2. An inhaler as claimed in claim 1, wherein the drug dosing device is arranged to provide a dose of powdered medicament entrained in a gasflow to the cyclone.

3. An inhaler as claimed in claim 1, wherein the chamber is comparable in volume to the cyclone.

4. An inhaler as claimed in claim 1, wherein the chamber has a volume of around 300 ml.

5. An inhaler as claimed in claim 2, wherein the chamber is comparable in volume to the cyclone.

6. An inhaler as claimed in claim 2, wherein the chamber has a volume of around 300 ml.

7. An inhaler as claimed in claim 3, wherein the chamber has a volume of around 300 ml.

* * * * *